(12) United States Patent
Gouliaev et al.

(10) Patent No.: US 7,632,948 B2
(45) Date of Patent: Dec. 15, 2009

(54) METHOD OF PREPARING ENANTIOMERS OF INDOLE-2,3-DIONE-3-OXIME DERIVATIVES

(75) Inventors: Alex H. Gouliaev, Veksjø Sj. (DK); William Dalby Brown, Søborg (DK); Frank Wätjen, Farum (DK)

(73) Assignee: NeuroSearch A/S, Ballerup (DK)

( * ) Notice: Subject to any disclaimer, the term of this patent is extended or adjusted under 35 U.S.C. 154(b) by 658 days.

(21) Appl. No.: 10/524,441

(22) PCT Filed: Aug. 13, 2003

(86) PCT No.: PCT/DK03/00539

§ 371 (c)(1), (2), (4) Date: Aug. 10, 2005

(87) PCT Pub. No.: WO2004/018466

PCT Pub. Date: Mar. 4, 2004

(65) Prior Publication Data

US 2006/0178391 A1    Aug. 10, 2006

(30) Foreign Application Priority Data

Aug. 22, 2002 (DK) ............................... 2002 01237

(51) Int. Cl.
*C07D 457/14* (2006.01)
(52) U.S. Cl. ...................................................... 546/80
(58) Field of Classification Search ........................ None
See application file for complete search history.

(56) References Cited

FOREIGN PATENT DOCUMENTS

| | | |
|---|---|---|
| EP | 0 439 779 A | 8/1991 |
| EP | 0 467 132 A | 1/1992 |
| WO | WO-98/14447 A | 4/1998 |
| WO | WO-01/18231 A | 3/2001 |

OTHER PUBLICATIONS

Nielsen et al., SPD 502: A Water-Soluble and In Vivo Long-Lasting AMPA Antagonist with Neuroprotective Activity, vol. 289, No. 3, 1999, pp. 1482-1501.

*Primary Examiner*—Rita J Desai
(74) *Attorney, Agent, or Firm*—Birch, Stewart, Kolasch & Birch, LLP

(57) ABSTRACT

The present invention is directed to a method of preparing enantiomers of indole-2,3-dione-3-oxime derivatives.

7 Claims, No Drawings

METHOD OF PREPARING ENANTIOMERS OF INDOLE-2,3-DIONE-3-OXIME DERIVATIVES

TECHNICAL FIELD

The present invention is directed to a method of preparing enantiomers of indole-2,3-dione-3-oxime derivatives.

BACKGROUND ART

Indole-2,3-dione-3-oxime derivatives are useful pharmaceutical products. WO 98/14447 (NeuroSearch) describes indole-2,3-dione-3-oxime derivatives useful for antagonising the effect of excitatory amino acids. These compounds are prepared by conventional methods of chemical synthesis including the step of reacting an 1H-indol-2,3-dion with an amino derivative. More specifically WO 98/14447 describes indole-2,3-dione-3-oxime derivatives, some of which exist as racemic mixtures.

It is often desirable, and sometimes subject to regulatory demands, to undertake drug development on specific enantiomers rather than racemic drugs. This rationale is based on the findings that often the desired characteristics of chiral compounds reside with one of its enantiomers, while the other enantiomer might in fact add to a potential toxicological effect of the drug.

In order to allow thorough investigation of each enantiomer, processes for obtaining enantiopure preparations of chiral compounds are of significant importance for drug development.

EP 439779 (Chisso Corp.) describes a process for producing optically active hydroxy lactones using enzymatic transesterification. However, a method of preparing enantiomers of indole-2,3-dione-3-oxime derivatives is not described.

EP 467132 (Chisso Corp.) describes 4-substituted-2-hydroxybutanoates and a process for producing them. However, a method of preparing enantiomers of indole-2,3-dione-3-oxime derivatives is not described.

SUMMARY OF THE INVENTION

The present invention is directed to a novel method for obtaining enantiopure preparations of chiral indole-2,3-dione-3-oxime derivatives.

Thus, in its first aspect, the invention provides a method of obtaining enantiopure preparations of chiral indole-2,3-dione-3-oxime derivatives (Compounds A or B), which method comprises the subsequent steps of (i) Reacting an 8-amino-1,2,3,4-tetrahydro-isoquinoline (Compound 9) derivative with chloral hydrate and hydroxylamine hydrochloride to give an N-(1,2,3,4-tetrahydro-isoquinolin-8-yl)-2-hydroxyimino-acetamide (Compound 10) derivative (Step 9);

(ii) Adding sulphuric acid to the N-(1,2,3,4-tetrahydro-isoquinolin-8-yl)-2-hydroxyimino-acetamide (Compound 10) derivative obtained in step (i) (Step 10); and (iii) Reacting the 2,3-dioxo-2,3,6,7,8,9-hexahydro-1H-pyrrolo[3,2-h]isoquinoline (Compound 11) derivative obtained in step (ii) with chiral (enantiopure (R) or (S)) α-N, N-diBoc-aminoxy-γ-butyrolactone to obtain the desired chiral end product, i.e. enantiopure (R)- or (S)-2-[2-oxo-1,2, 6,7,8,9-hexahydro-pyrrolo[3,2-h]isoquinolin-3-ylideneaminooxy]4-hydroxy-butyric acid) (Compound A or B) (Step 11);

followed by recovery of the desired end product.

In another aspect the invention provides a method of preparing the enantiopure starting material for use according to the method of the invention which method comprises the subsequent steps of (i) acetylating a racemic mixture of α-hydroxy-γ-butyrolactone to obtain racemic α-acetoxy-γ-butyrolactone (Step 1);

(ii) subjecting the racemic α-acetoxy-γ-butyrolactone obtained in step (i) to enzymatic de-acetylation to obtain enantiopure (S) or (R) α-acetoxy-γ-butyrolactone (Step 2); and (iii) subjecting the enantiopure (S) or (R) α-acetoxy-γ-butyrolactone obtained in step (ii) to hydrolysis using acidic ion-exchange (Step 3);

followed by recovery of the desired end product.

Other objects of the invention will be apparent to the person skilled in the art from the following detailed description and examples.

DETAILED DISCLOSURE OF THE INVENTION

The Indole-2,3-dione-3-oxime Derivatives

The present invention provides a method of preparing enantiomers of indole-2,3-dione-3-oxime derivatives. The indole-2,3-dione-3-oxime derivatives obtained according to the method of the invention may in particular be characterised by the general Formula IA or IB

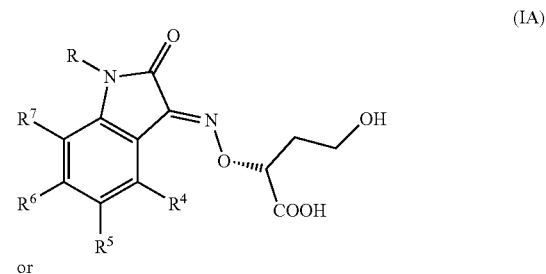

(IA)

or

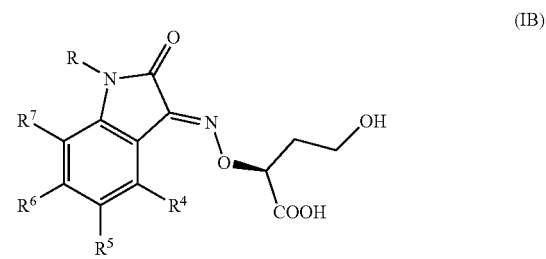

(IB)

wherein

R represents hydrogen, alkyl or benzyl; and $R^4$ represent hydrogen or alkyl; and $R^5$ represents phenyl, which phenyl may optionally be substituted one or more times with substituents selected from the group consisting of halogen, $CF_3$, $NO_2$, CN, $NH_2$, alkyl, alkoxy and $SO_2NR^{51}R^{52}$; wherein $R^{51}$ and $R^{52}$, independently of each another represent hydrogen or alkyl; or $R^{51}$ and $R^{52}$ together with the N-atom to which they are attached form a piperidinyl- or morpholinyl-ring; and $R^6$ and $R^7$ together form a benzo-fused ring of the formula

—$NR^8$—$CH_2$—$CH_2$—$CH_2$—;

—$CH_2$—$NR^8$—$CH_2$—$CH_2$—;

—$CH_2$—$CH_2$—$NR^8$—$CH_2$—; or

—$CH_2$—$CH_2$—$CH_2$—$NR^8$—;

wherein $R^8$ represents hydrogen or alkyl.

In a more preferred embodiment the indole-2,3-dione-3-oxime derivative obtained according to the method of the invention is characterised by Formula IIA or IIB

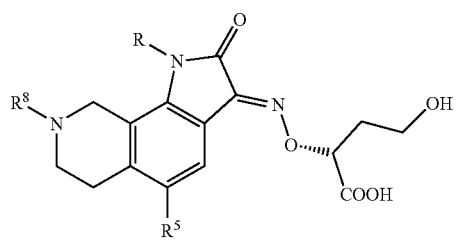
(IIA)

or

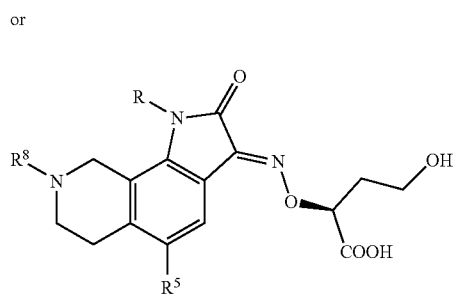
(IIB)

wherein

R represents hydrogen or alkyl;

$R^5$ represents phenyl, which phenyl is optionally substituted with halogen, $CF_3$, $NO_2$, CN or $SO_2NR^{51}R^{52}$; wherein $R^{51}$ and $R^{52}$, independently of each another represent hydrogen or alkyl; or $R^{51}$ and $R^{52}$ together with the N-atom to which they are attached form a piperidinyl- or morpholinyl-ring; and $R^8$ represents hydrogen or alkyl.

In an even more preferred embodiment the indole-2,3-dione-3-oxime derivative obtained according to the method of the invention is characterised by Formula IIIA or IIIB

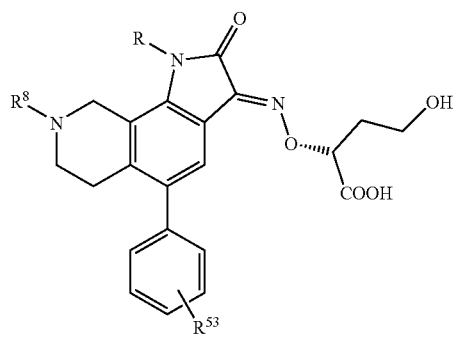
(IIIA)

or

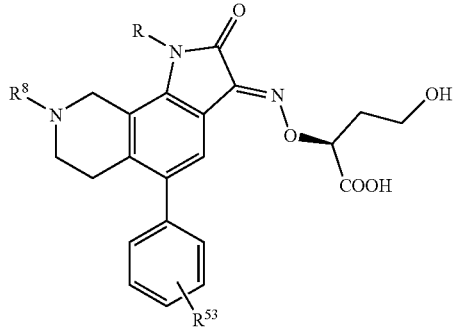
(IIIB)

wherein

R represents hydrogen or alkyl;

$R^{53}$ represents $SO_2NR^{51}R^{52}$; wherein $R^{51}$ and $R^{52}$, independently of each another represent hydrogen or alkyl; or $R^{51}$ and $R^{52}$ together with the N-atom to which they are attached form a piperidinyl- or morpholinyl-ring; and $R^8$ represents hydrogen or alkyl.

In an even more preferred embodiment the indole-2,3-dione-3-oxime derivative obtained according to the method of the invention is characterised by the general Formula IIIA or IIIB, wherein R represents hydrogen or $C_{1-3}$-alkyl;

$R^{53}$ represents $SO_2NR^{51}R^{52}$; wherein $R^{51}$ and $R^{52}$, independently of each another represent hydrogen or $C_{1-3}$-alkyl; or $R^{51}$ and $R^{52}$ together with the N-atom to which they are attached form a piperidinyl- or morpholinyl-ring; and $R^8$ represents hydrogen or $C_{1-6}$-alkyl.

In a most preferred embodiment the indole-2,3-dione-3-oxime derivative obtained according to the method of the invention is Compound IVA or IVB

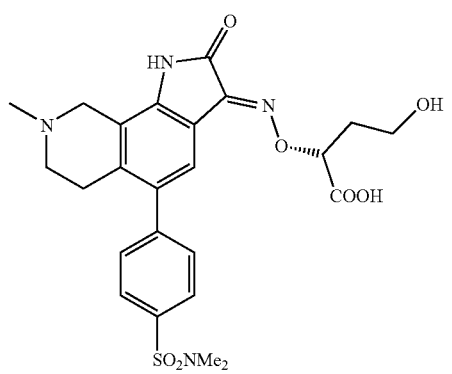
(IVA)

or

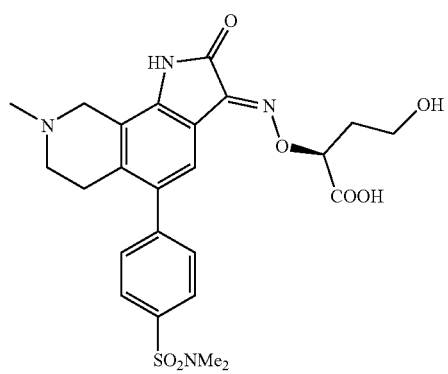

(IVB)

The Method of Obtaining Enantiopure Preparations of Chiral Indole-2,3-dione-3-oxime Derivatives The present invention provides a method of preparing enantiomers of indole-2,3-dione-3-oxime derivatives, in particular the indole-2,3-dione-3-oxime derivatives described above.

In a preferred embodiment the method of the invention comprises the subsequent steps of (i) Reacting an 8-amino-1,2,3,4-tetrahydro-isoquinoline (Compound 9) derivative with chloral hydrate and hydroxylamine hydrochloride to give an N-(1,2,3,4-tetrahydro-isoquinolin-8-yl)-2-hydroxyimino-acetamide (Compound 10) derivative (Step 9);

(ii) Adding sulphuric acid to the N-(1,2,3,4-tetrahydro-isoquinolin-8-yl)-2-hydroxyimino-acetamide (Compound 10) derivative obtained in step (i) (Step 10); and (iii) Reacting the 2,3-dioxo-2,3,6,7,8,9-hexahydro-1H-pyrrolo[3,2-h]isoquinoline (Compound 11) derivative obtained in step (ii) with chiral (enantiopure (R) or (S)) α-N,N-diBoc-aminoxy-γ-butyrolactone to obtain the desired chiral end product, i.e. enantiopure (R)- or (S)-2-[2-oxo-1,2,6,7,8,9-hexahydro-pyrrolo[3,2-h]isoquinolin-3-ylideneaminooxy]-4-hydroxy-butyric acid) (Compound A or B) (Step 11);

followed by recovery of the desired end product.

In a preferred embodiment the method further comprises the step of (a) reacting enantiopure (S) or (R) α-hydroxy-γ-butyrolactone with N,N-diBoc-hydroxylamine to give enantiopure (S) or (R) α-N,N-diBoc-aminoxy-γ-butyrolactone (Step 8a);

followed by steps (i) to (iii) as described above.

In another preferred embodiment the method further comprises the step of (b) subjecting N,N-diBoc-O-benzylhydroxylamine to hydrogenation to give N,N-diBoc-hydroxylamine (Step 7);

followed by step (a) and steps (i) to (iii) as described above.

In a third preferred embodiment the method further comprises the step of (c) converting O-benzylhydroxylamine into N,N-diBoc-O-benzylhydroxylamine using Boc$_2$O (Step 6);

followed by step (b), step (a), and steps (i) to (iii) as described above.

In a fourth preferred embodiment the method further comprises the step of (d) reacting enantiopure (S) or (R) α-hydroxy-γ-butyrolactone with tosyl chloride to give enantiopure (S) or (R) α-tosyloxy-γ-butyrolactone (Step 5);

followed by step (c), step (b), step (a), and steps (i) to (iii) as described above.

In a most preferred embodiment the 8-amino-1,2,3,4-tetrahydro-isoquinoline (Compound 9) derivative of step (i) is 4-(8-amino-2-methyl-1,2,3,4-tetrahydro-isoquinolin-5-yl)-N,N-dimethyl-benzenesulfonamide (to obtain N-[5-(4-dimethylsulfamoyl-phenyl)-2-methyl-1,2,3,4-tetrahydro-isoquinolin-8-yl]-2-hydroxyimino-acetamide); and the 2,3-dioxo-2,3,6,7,8,9-hexahydro-1H-pyrrolo[3,2-h]isoquinoline (Compound 11) derivative of step (iii) is N,N-dimethyl-4-(8-methyl-2,3-dioxo-2,3,6,7,8,9-hexahydro-1H-pyrrolo[3,2-h]isoquinolin-5-yl)-benzenesulfonamide;

giving enantiopure (R)- or (S)-2-[5-(4-dimethylsulfamoyl-phenyl)-8-methyl-2-oxo-1,2,6,7,8,9-hexahydro-pyrrolo[3,2-h]isoquinolin-3-ylideneaminooxy]-4-hydroxy-butyric acid as the end product (Compound A or B).

Preparation of the Starting Materials

In another aspect the invention provides a method of producing the enantiopure starting materials for use according to the method described above.

The method of the invention for preparing the starting materials is characterised by comprising the subsequent steps of (i) acetylating a racemic mixture of α-hydroxy-γ-butyrolactone to obtain racemic α-acetoxy-γ-butyrolactone (Step 1);

(ii) subjecting the racemic α-acetoxy-γ-butyrolactone obtained in step (i) to enzymatic de-acetylation to obtain enantiopure (S) or (R) α-acetoxy-γ-butyrolactone (Step 2); and (iii) subjecting the enantiopure (S) or (R) α-acetoxy-γ-butyrolactone obtained in step (ii) to hydrolysis using acidic ion-exchange (Step 3);

followed by recovery of the desired end product, i.e. the enantiopure (S) or (R) α-hydroxy-γ-butyrolactone.

In a preferred embodiment the method further comprises the step of (iv) subjecting the enantio-impure remainings of step (iii), i.e. the enantio-impure α-hydroxy-γ-butyrolactone and α-acetoxy-γ-butyrolactone, to racemisation using acid or base;

followed by re-entry of the racemic mixture into step (i).

In a more preferred embodiment the enzymatic de-acetylation of step (ii) is carried out using a lipolytic enzyme. In a most preferred embodiment the lipolytic enzyme is Lipase PS (available from Amano Pharmaceutical Co.).

EXAMPLE

The invention is further illustrated with reference to the following example, which is not intended to be in any way limiting to the scope of the invention as claimed.

First the synthetic route to the optical isomers of 2-[5-(4-dimethylsulfamoyl-phenyl)-8-methyl-2-oxo-1,2,6,7,8,9-hexahydro-pyrrolo[3,2-h]isoquinolin-3-ylideneaminooxy]-4-hydroxy-butyric acid, hereinafter designated Compounds IVA and IVB, is outlined.

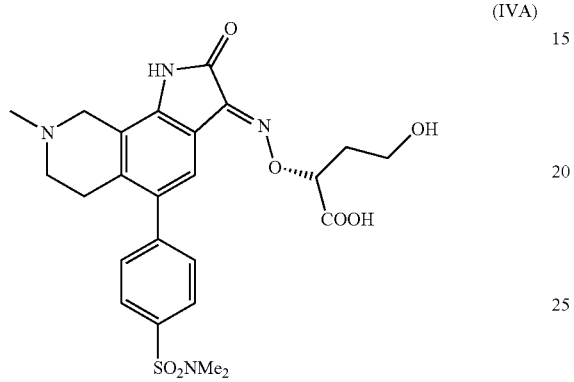
(IVA)

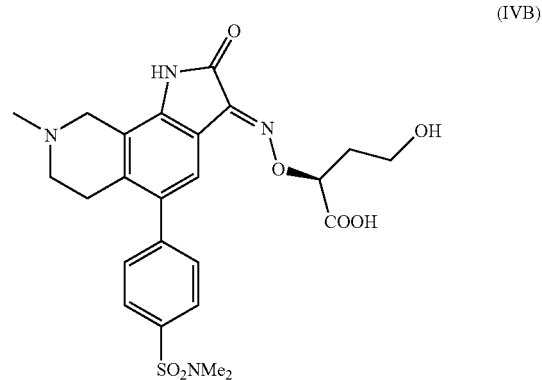
(IVB)

Synthesis of the Chiral Building Blocks

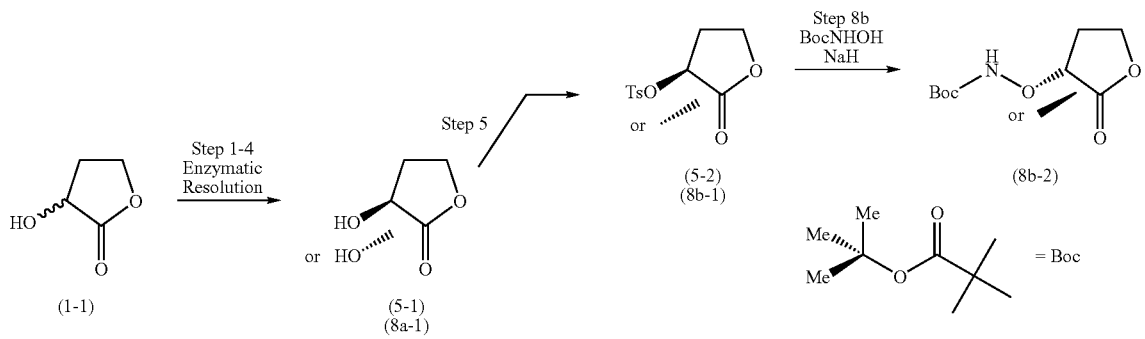

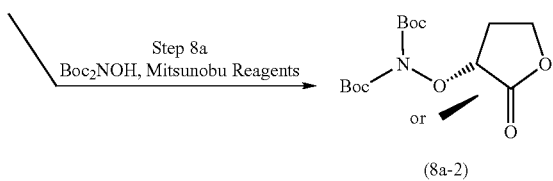

Synthesis of the N,N-DiBoc Protected Hydroxylamine Part
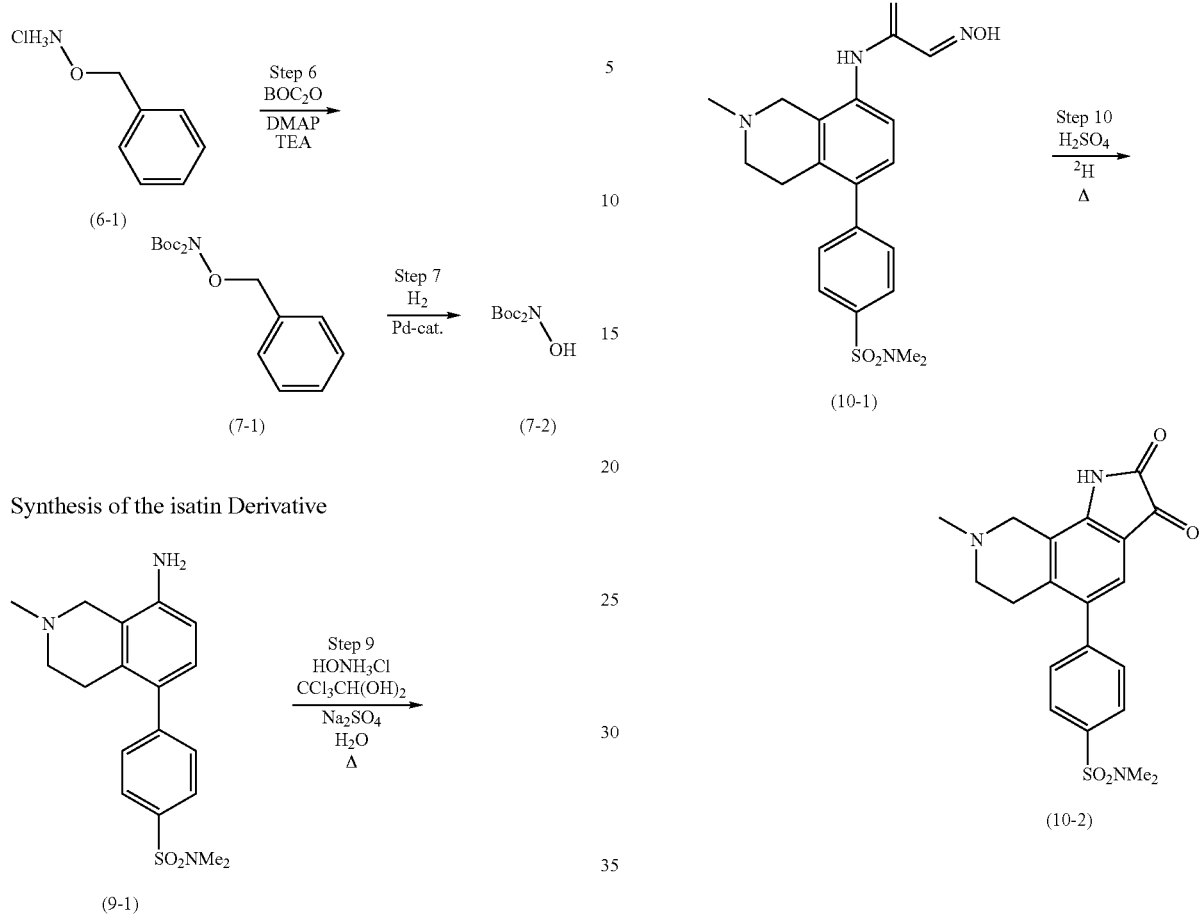
Synthesis of the isatin Derivative
Synthesis of Enantiopure (R)-E-1 and (S)-E-1
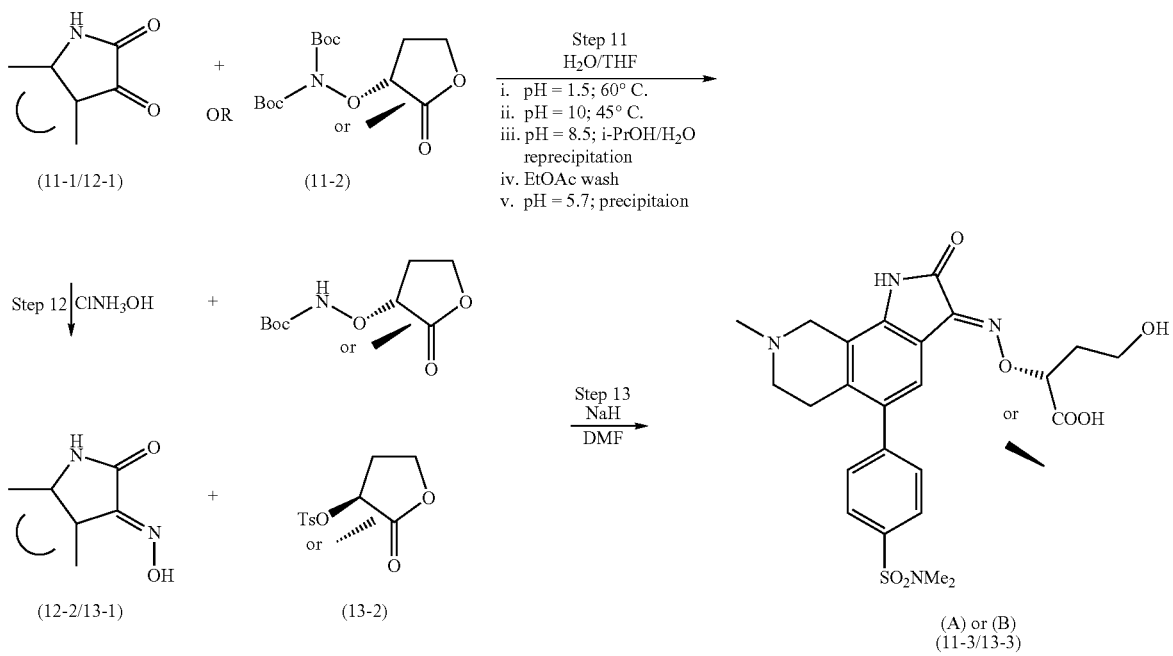

Next, a more detailed description of each step of the synthesis is presented.

Step 1

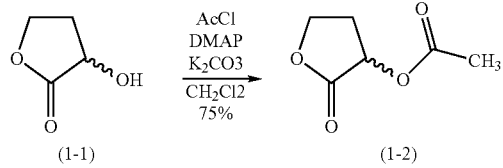

A mixture of racemic α-hydroxy-γ-butyrolactone (25 g; 0.25 mol), DMAP (1.5 g), acetylchloride (25.5 ml; 0.37 mol) in CH₂Cl₂ (325 mL) was added solid K₂CO₃ (50 g) in portions (slightly exothermic). The reaction mixture was stirred at room temperature overnight, filtered and evaporated to dryness. Column chromatography (Petrol ether 80-100: EtOAc=2:1) gave 26.4 g (75%) racemic α-acetoxy-γ-butyrolactone.

Step 2

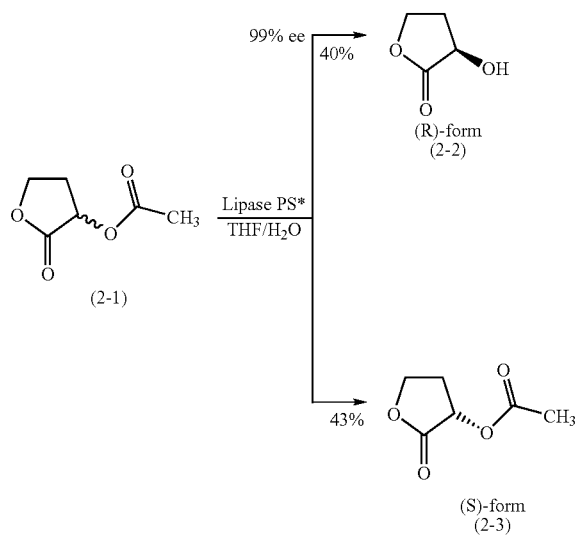

A mixture of racemic α-acetoxy-γ-butyrolactone (29.8 g; 0.207 mol) and Amano's Lipase PS (800 mg) in THF/water (200 mL; 10/1) was stirred at room temperature overnight. The reaction mixture was filtered and evaporated to dryness. The crude product was dissolved in CH₂Cl₂ (250 mL) and extracted with cold water (5×50 mL). The organic phase was dried (MgSO₄), filtered and evaporated to dryness to yield 12.6 g (43%) enantiopure (S)-α-acetoxy-γ-butyrolactone.

The combined aqueous phases were washed with CH₂Cl₂ (5×50 mL). The aqueous phase was evaporated to dryness, added CH₂Cl₂, dried (MgSO₄), filtered and evaporated to dryness to give 8.5 g (40%) (R)-α-hydroxy-γ-butyrolactone. Overall yield by moles; 83%. $[\alpha]_D^{25}=+65.7°$.

Step 3

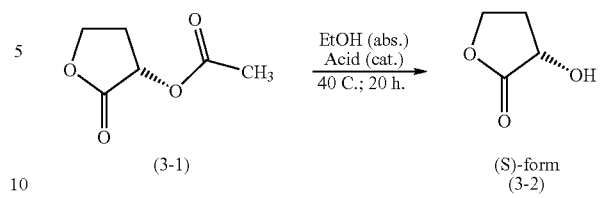

A suspension of enantiopure (S)-α-acetoxy-γ-butyrolactone (5 g, 34.7 mmol) and Amberlite IRA120 (acid form) in H₂O (50 mL) was heated to reflux and reaction progress monitored by GCMS. After 2 hours, GCMS indicated complete transformation. The reaction mixture was filtered and evaporated to dryness. Vacuum distillation 0.3-0.4 mbar (b.p. 85-92° C.) afforded the enantiopure (S)-α-hydroxy-γ-butyrolactone (2.6 g, 76% yield). $[\alpha]_D^{25}=-66.1°$.

The crude product may also be isolated from the aqueous solution by extraction with CH₂Cl₂ and the pure product alternatively be isolated by column chromatography. Amberlite IRA-120 may be substituted by H₂SO₄, however with an overall lower yield.

Step 4

Enantio-impure remainings of α-hydroxy-γ-butyrolactone and α-acetoxy-γ-butyrolactone from step 3 may be recycled by racemisation using acid or base, followed by re-entry into steps 1 to 3.

Step 5

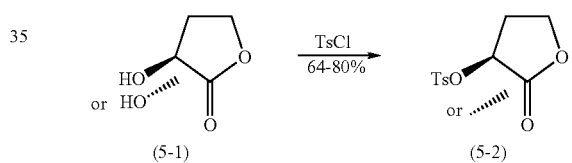

A suspension of (R)-α-hydroxy-γ-butyrolactone (3.5 g, 34.3 mmol), tosyl chloride (10.0 g, 52.6 mmol), and K₂CO₃ (2.23 g, 16.2 mmol) in dry CH₂Cl₂ (50 mL) was stirred at room temperature overnight. The reaction mixture was filtered, and the filtrate washed with 1M phosphate buffer pH=7 (2×50 mL), 3 M NaCl (aq.) (1×50 mL), dried with Na₂SO₄, filtered and evaporated to dryness to give the crude product. The crude product was triturated by PE40/60 (50 mL) and stirred for 30 minutes. The precipitate formed was isolated by filtration and washed with PE40/60 to remove trace amounts of tosyl chloride, to give 7.7 g (87%) of enantiopure (R)-α-tosyloxy-γ-butyrolactone. $[\alpha]_{365}^{25}=-9.9°$.

The (S)-isomer was prepared similarly. $[\alpha]_{365}^{25}=+9.8°$.

Step 6

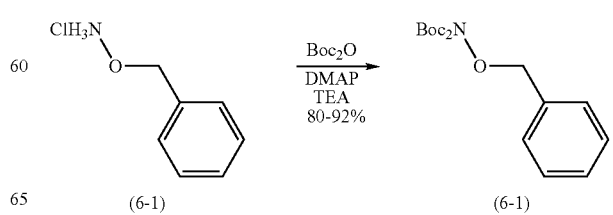

A suspension of O-benzylhydroxylamine hydrochloride (30 g, 188 mmol) in acetonitrile (150 mL) was added triethylamine (29 mL). The thick suspension was stirred for 60 minutes at room temperature and filtered. The precipitate was washed with acetonitrile (100 mL) on the filter. The combined filtrates were added to a cooled (0° C.) solution of $Boc_2O$ (45 g, 207 mmol) in acetonitrile (150 ml), over 20 minutes. The reaction mixture was stirred at 0° C., and allowed slowly to warm up to room temperature. The reaction mixture was left with stirring at room temperature overnight, when $^1$H-NMR indicated complete conversion of O-benzylhydroxylamine into N-Boc-O-benzylhydroxylamine.

The reaction mixture was added a solution of $Boc_2O$ (6.7 g, 310 mmol) in acetonitrile (150 mL), followed by a solution of DMAP (2 g, 16.4 mmol) in acetonitrile (30 mL). The reaction mixture was then stirred at 40° C. until TLC (EtOAc:PE60/80=1:5) indicated complete conversion of the intermediate N-Boc-O-benzylhydroxylamine (approx. 2 hours). The reaction mixture was evaporated to dryness and re-dissolved in EtOAc (200 mL). The organic phase was washed with a mixture of 1M phosphate buffer pH=7 (100 mL) and NaCl (aq., sat.) (50 mL). The organic phase was dried with $Na_2SO_4$, filtered and evaporated to dryness to give an oil, which precipitated upon trituration by PE40/60 (20 mL). The precipitated was isolated by filtration to give 56 g (92%) of N,N-diBoc-O-benzylhydroxylamine as a white solid.

Step 7

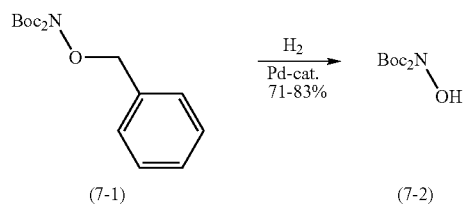

(7-1)    (7-2)

A suspension of N,N-diBoc-O-benzylhydroxylamine (15 g, 46.4 mmol) and 5% Pd/C (0.9 g) in 96% EtOH was subjected to hydrogenation at atmospheric pressure. When 390 mL $H_2$ was consumed, hydrogenation was stopped. The reaction mixture was filtered through celite and evaporated to dryness to give 12.5 g of an orange oil composed of N,N-diBoc-hydroxylamine and N,N-diBoc-imide (86:14).

The oil was dissolved in EtOAc (25 mL) and extracted with 1M NaOH (3×25 mL). The combined aqueous phases were immediately poured into a 1M phosphate buffer pH=7 and extracted with EtOAc (3×75 mL). The combined organic fractions were dried with $Na_2SO_4$, filtered and evaporated to dryness. The isolated white solid was air dried to give 8.8 g (81%) of pure N,N-diBoc-hydroxylamine.

Step 8a

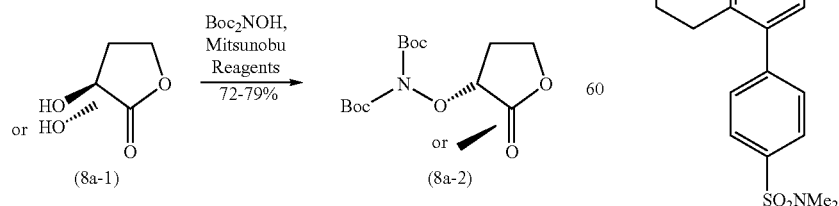

(8a-1)    (8a-2)

A solution of N,N-diBoc-hydroxylamine (8.5 g, 36 mmol) in dry THF (50 mL) under $N_2$ was added $Ph_3P$ (11 g, 42 mmol) and cooled to 0° C. A solution of (S)-α-hydroxy-γ-butyrolactone (3.6 g, 35 mmol) in dry THF (10 mL) was added, followed by addition of DEAD (6.8 ml, 42 mmol) during 30 minutes. The dark reaction mixture was stirred at 0° C. until TLC (EtOAc:PE60/80=1:2, $KMnO_4$ spray) indicated complete conversion of (S)-α-hydroxy-γ-butyrolactone (approx. 2 hours).

The reaction mixture was evaporated to dryness, dissolved in $Et_2O$ (50 mL) and triturated by addition of PE40/60 (100 mL). The reaction mixture was filtered, and the precipitate thoroughly washed with $Et_2O$:PE40/60=1:1 (100 mL). The combined organic filtrates were evaporated to dryness to give 16 g of brown oil. The oil was subjected to column chromatography. (1000 mL $SiO_2$, 7 cm in diameter, eluent: EtOAc:PE60/80=1:2). The pure fractions were combined, evaporated to dryness and washed with PE40/60 (15 mL) to give 8.5 g (77%) of enantiopure (R)-α-N,N-diBoc-aminoxy-γ-butyrolactone.

(R)-isomer: $[\alpha]_D^{25}=+62.5°$; $[\alpha]_{365}^{25}=+210°$.

The (R)-isomer was prepared similarly: $[\alpha]_D^{25}=-62.8°$; $[\alpha]_{365}^{25}=-211°$.

Step 8b

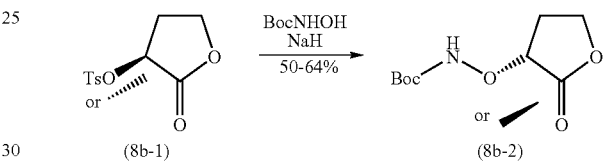

(8b-1)    (8b-2)

A suspension of 60% NaH (350 mg, 8.8 mmol) in dry $CH_2Cl_2$ under $N_2$ at 0° C. was added a solution of BocNHOH in $CH_2Cl_2$ (5 mL). The reaction mixture was stirred at 0° C. for 30 minutes, where after a solution of (R)-α-tosyloxy-γ-butyrolactone (2 g, 7.8 mmol) in $CH_2Cl_2$ (5 mL) was added. The reaction mixture was allowed to warm up to room temperature, and left with stirring overnight. The reaction mixture was quenched with 1M phosphate buffer pH=6.3 (20 mL) and the organic phase separated. The aqueous phase was extracted with $CH_2Cl_2$ (2×20 mL), and the combined organic fractions extracted with NaCl (aq., sat.) (15 mL). The organic fraction was dried with $Na_2SO_4$, filtered and evaporated to dryness. Column chromatography (150 g $SiO_2$, eluent: EtOAc:PE60/80=1:2) gave 1.5 g (89%) of (S)-α-N-Boc-aminoxy-γ-butyrolactone. $[\alpha]_D^{25}=-42°$; $[\alpha]_{365}^{25}=-127°$.

In a similar way the (R)-isomer, containing approximately 10% of (S)-isomer, was prepared: $[\alpha]_{365}^{25}=+70°$.

Steps 9-10

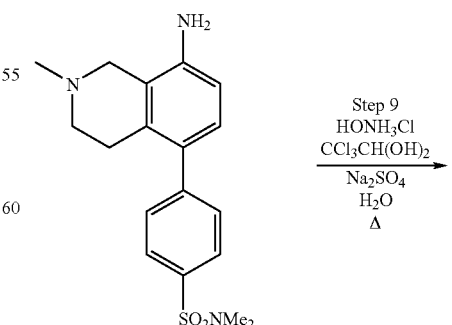

(9-1)

Purification

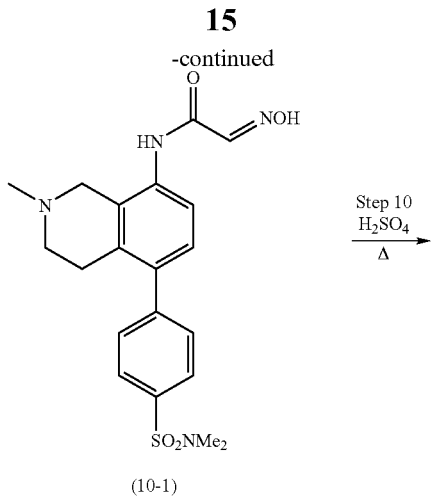

(10-1)

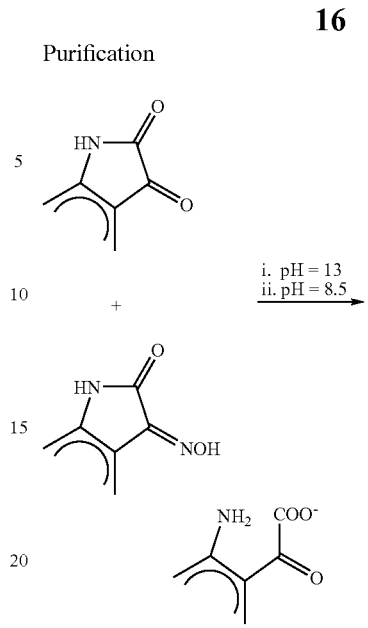

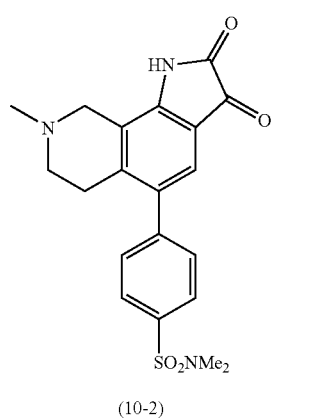

(10-2)

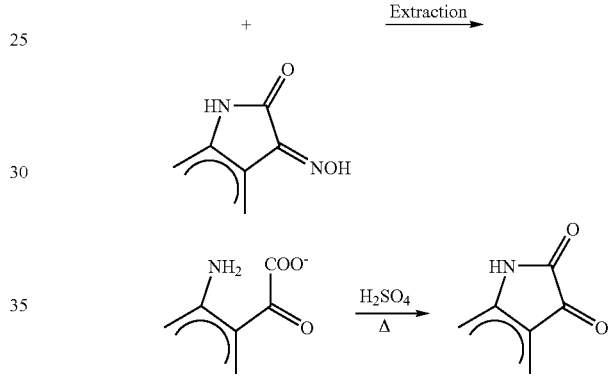

+

9-11%
(10-3)

Chloral hydrate (71.6 g, 0.434 mol), hydroxylamine hydrochloride (60.3 g, 0.868 mol) and $Na_2SO_4$ (243.3 g, 1.65 mol) were added in sequence to a reaction vessel containing $H_2O$ (1.8 L) preheated to 80° C. When a clear solution was achieved, the aniline (4-(8-amino-2-methyl-1,2,3,4-tetrahydro-isoquinolin-5-yl)-N,N-dimethyl-benzenesulfonamide; 99.0 g, 0.217 mol) was added. The reaction was stirred for 45 minutes when TLC showed full consumption of the aniline. Celite (39 g) was added and the reaction mixture was cooled to 40° C. and stirred for 1 hour. The reaction mixture was filtered and the precipitate washed with cold $H_2O$ (500 mL). The isolated solid material (isonitrosoacetanilide on celite) was dried under a heating lamp to give 132 g material, which was used without further purification.

The crude isonitrosoacetanilide derivative (N-[5-(4-dimethylsulfamoyl-phenyl)-2-methyl-1,2,3,4-tetrahydro-isoquinolin-8-yl]-2-hydroxyimino-acetamide) obtained above was added over 45 minutes to a solution of $H_2SO_4$ (350 mL), preheated to 75° C. During the addition, the reaction temperature increased to 80-85° C. After complete addition, the reaction was stirred for another 30 minutes at a reaction temperature of 75-85° C., when all the isonitrosoacetanilide was consumed (TLC, $CH_2Cl_2$:acetone:MeOH=4:1:1).

The reaction mixture (i.e. N,N-dimethyl-4-(8-methyl-2,3-dioxo-2,3,6,7,8,9-hexahydro-1H-pyrrolo[3,2-h]isoquinolin-5-yl)-benzenesulfonamide and 4-(3-hydroxyimino-8-methyl-2-oxo-2,3,6,7,8,9-hexahydro-1H-pyrrolo[3,2-h]isoquinolin-5-yl)-N,N-dimethyl-benzenesulfonamide) was poured onto H₂O (3.5 L), heated to reflux and then filtered warm to remove celite. The celite was washed with boiling water (750 mL), and the combined aqueous fractions allowed cooling slowly overnight for precipitation. The precipitate was filtered off, washed with H₂O (2×250 mL) and 96% EtOH (2×250 mL) and then air dried to give 69.8 g (67%) of crude isatin derivative as the hydrosulfate. The crude product contained 11.4% (typically 9-13%) of the oxime.

Crude product (38.1 g, 76.7 mmol) was suspended in H₂O (800 mL) and pH adjusted to 13 using 4 M NaOH (approx. 80 mL) to give a purple solution, which was stirred for 20 minutes. The then yellow-orange solution was added THF (300 mL) and pH adjusted to 8.5 using AcOH. This solution was washed with EtOAc (4×400 mL), then added conc. H₂SO₄ (90 mL) and heated to 75° C. The aqueous solution was allowed to slowly cool to room temperature and then 0° C. The precipitate formed was filtered off, then washed with H₂O (2×100 mL) and 96% EtOH (2×100 mL) to give 31.3 g (corresponding to approx. 53% yield from the aniline) of the pure isatin derivative as the hydrosulfate.

Step 11

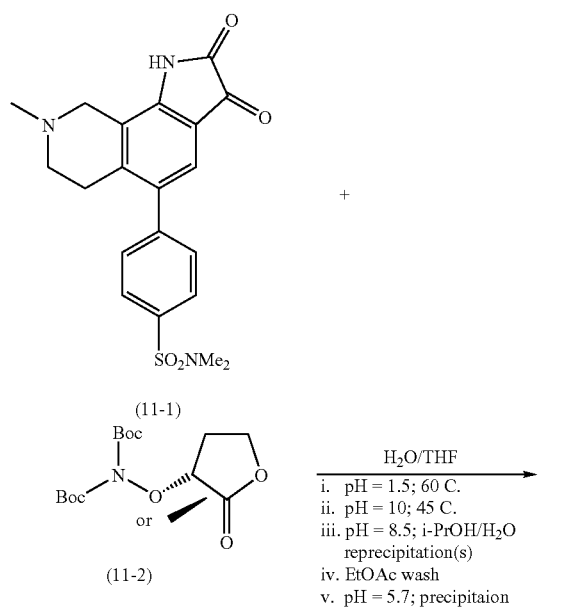

A suspension of the isatin derivative (i.e. N,N-dimethyl-4-(8-methyl-2,3-dioxo-2,3,6,7,8,9-hexahydro-1H-pyrrolo[3,2-h]isoquinolin-5-yl)-benzenesulfonamide) as the hydrosulfate (32.5 g, 65.4 mmol) was suspended in H₂O (650 mL). The reaction mixture was heated to 60° C. and pH adjusted to 1.5 using 2M H₂SO₄ (aq.). A solution of (R)- or (S)-α-N,N-diBoc-aminoxy-γ-butyrolactone (23 g, 72.5 mmol) in THF (130 mL) was added. The thick reaction mixture was stirred at 60° C. for 9 hours, when HPLC indicated complete consumption of the isatin derivative.

The reaction mixture was left overnight at room temperature, warmed to 40° C. and pH adjusted to 10 using 1M NaOH (aq.) (approx. 150 mL). Further 1M NaOH (aq.) (approx. 180 mL overall) was added during the reaction to keep pH at 10. After stirring for 4 hours at 40° C., the reaction mixture became a nearly clear solution. HPLC indicated that all product, in intermediate lactone form was consumed, and pH was adjusted to 8.5 using 2M H₂SO₄ (aq.).

The reaction mixture was evaporated to dryness to yield 40.3 g solid. The isolated solid was refluxed in a mixture of i-PrOH/H₂O (85/15) (1600 mL) and filtered warm (inorganic salts are removed). The filtrate was allowed to slowly cool to 0° C., and left overnight. The precipitate formed, was isolated by filtration to give 23.9 g yellow to orange crystals. The crystals (20 g) was dissolved in H₂O (80 mL) and stirred vigorously with EtOAc (250 mL) for 1½ hour (to remove the Z-isomer and remainings of the isatin oxime). The organic phase was discarded, and the aqueous phase was evaporated to dryness. The solid material isolated was suspended in THF (400 mL) and filtered.

The precipitate was dissolved in H₂O (160 mL) and pH adjusted slowly to 5.2 using 2M H₂SO₄ (aq.). The mixture was stirred 1½ hour at room temperature and filtered. The isolated solid was washed with cold H₂O (2×25 mL) and air dried to give A or B (i.e. (R)- or (S)-2-[5-(4-dimethylsulfamoyl-phenyl)-8-methyl-2-oxo-1,2,6,7,8,9-hexahydro-pyrrolo[3,2-h]isoquinolin-3-ylideneaminooxy]-4-hydroxy-butyric acid) as a yellow amorphous solid, 15.8 g (56%). The reaction occurs with retention of stereochemistry, i.e. no inversion is observed.

Step 12

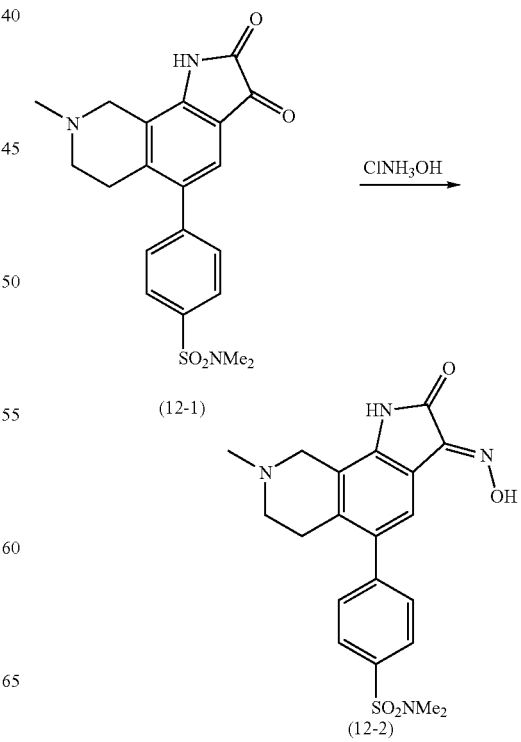

A suspension of isatin derivative 12-1 (i.e. N,N-dimethyl-4-(8-methyl-2,3-dioxo-2,3,6,7,8,9-hexahydro-1H-pyrrolo[3,2-h]isoquinolin-5-yl)-benzenesulfonamide) as the hydrosulfate (3.5 g, 7 mmol) in 96% EtOH (100 ml) was added hydroxylammonium chloride (1 g, 14 mmol) and then refluxed for 2½ hours. As the starting material was not completely consumed (TLC), further hydroxylammonium chloride (0.3 g, 2.1 mmol) was added. The reaction mixture was left at reflux over night.

The reaction mixture was cooled and filtered, and the precipitate washed with 96% EtOH. The precipitate was suspended in H$_2$O (100 ml), warmed to 75-80° C. and pH adjusted to 8.5 using 4 M NaOH (aq.). The aqueous solution was cooled to rt. and filtered. The precipitate was washed with H$_2$O, then suspended in abs. EtOH (100 ml) and brought to reflux. The solution was cooled to room temperature and filtered.

The precipitate was washed with abs. EtOH and air dried to give 2.63 g (91%) of 12-2 (i.e. 8-methyl-5-(4-(N,N-dimethylsulphamoyl)-phenyl)-6,7,8,9-tetrahydro-1H-pyrrolo-[3,2-h]-isoquinoline-2,3-dione-3-oxime) as the free base. The free base darkens upon standing but may be stored as the hydrosulfate.

Step 13

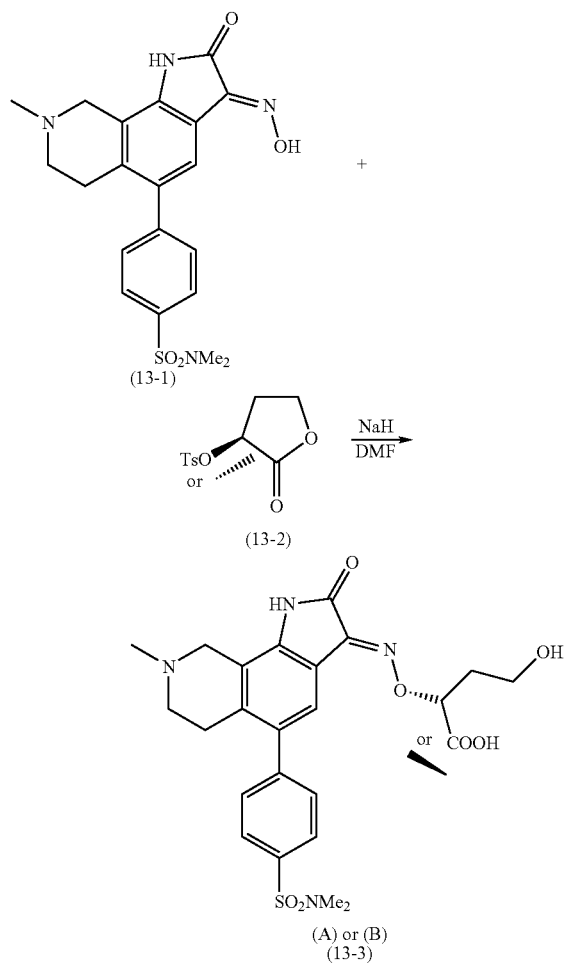

A suspension of 60% NaH (50 mg, 1.25 mmol) in dry DMF (2 ml) under N$_2$ at 0° C. was slowly added a solution of the isatin oxime, 8-methyl-5-(4-(N,N-dimethylsulphamoyl)-phenyl)-6,7,8,9-tetrahydro-1H-pyrrolo-[3,2-h]-isoquinoline-2,3-dione-3-oxime (500 mg, 1.25 mmol) in dry DMF (8 ml). The reaction mixture was stirred for 30 minutes at 0° C., where after a solution of (R)-α-tosyloxy-γ-butyrolactone (340 mg, 1.33 mmol) in dry DMF (2 ml) was added. The reaction was left with stirring at room temperature overnight, when HPLC indicated complete consumption of the isatin oxime.

The reaction mixture was evaporated to dryness and then added H$_2$O (20 ml) and dioxane (5 ml). The reaction mixture was adjusted to pH=10 by use of 1M NaOH. Further NaOH was added to keep the pH at 10. The reaction mixture was left with stirring over night at room temperature and heated to 40-45° C. for 1 hour, when HPLC indicated complete conversion of the intermediate lactone. The reaction mixture was adjusted to pH=8.5 and evaporated to dryness (extensive foaming).

The isolated solid was refluxed in i-PrOH (15 ml) for 5 minutes, cooled to room temperature and filtered to give 610 mg of solid material. Part of the solid material (550 mg) was refluxed in a mixture of i-PrOH (15 ml) and H$_2$O (0.75 ml) and cooled to 0° C. The precipitate formed was isolated by filtration to give 310 mg of crude material.

The mother liquor was mainly composed of sodium tosylate. The crude material (300 mg) was dissolved in H$_2$O (10 ml) and pH adjusted to 5.7 using 1M HCl, alternatively 5.2 using 2M H$_2$SO$_4$ (aq.). An oil separates and H$_2$O was removed be decantation. The product precipitates upon trituration by EtOH. The product was isolated by filtration, giving 160 mg (28%) of IVA or IVB (i.e. (R)- or (S)-2-[5-(4-dimethylsulfamoyl-phenyl)-8-methyl-2-oxo-1,2,6,7,8,9-hexahydro-pyrrolo[3,2-h]isoquinolin-3-ylideneaminooxy]-4-hydroxy-butyric acid).

The reaction occurs with inversion of stereochemistry, i.e. the stereocenter in α-tosyloxy-γ-butyrolactone is inverted.

The invention claimed is:

1. A method of preparing the chiral (±) isomers of indole-2,3-dione-3-oxime compounds, which method comprises the sequential steps of:
   (i) reacting an 8-amino-1,2,3,4-tetrahydro-isoquinoline with chloral hydrate and hydroxylamine hydrochloride to give an N-(1,2,3,4-tetrahydro-isoquinolin-8-yl)-2-hydroxyimino-acetamide;
   (ii) adding sulphuric acid to the N-(1,2,3,4-tetrahydro-isoquinolin-8-yl)-2-hydroxyimino-acetamide obtained in step (i) to provide a 2,3-dioxo-2,3,6,7,8,9-hexahydro-1H-pyrrolo[3,2-h]isoquinoline; and
   (iii) reacting the 2,3-dioxo-2,3,6,7,8,9-hexahydro-1H-pyrrolo[3,2-h]isoquinoline obtained in step (ii) with chiral (enantiopure (R) or (S)) α-N,N-diBoc-aminoxy-γ-butyrolactone to obtain the desired chiral end product, i.e. enantiopure (R)- or (S)-2-[2-oxo-1,2,6,7,8,9-hexahydro-pyrrolo[3,2-h]isoquinolin-3-ylideneaminooxy]-4-hydroxy-butyric acid.

2. The method of claim 1, which method further comprises the step of
   (a) reacting enantiopure (S) or (R) α-hydroxy-γ-butyrolactone with N,N-diBoc-hydroxylamine to give enantiopure (S) or (R) α-N,N-diBoc-aminoxy-γ-butyrolactone;
   followed by the sequential steps of:
   (i) reacting an 8-amino-1,2,3,4-tetrahydro-isoquinoline with chloral hydrate and hydroxylamine hydrochloride to give an N-(1,2,3,4-tetrahydro-isoquinolin-8-yl)-2-hydroxyimino-acetamide;
   (ii) adding sulphuric acid to the N-(1,2,3,4-tetrahvdro-isoquinolin-8-yl)-2-hydroxyimino-acetamide obtained in step (i) to provide a 2,3-dioxo-2,3,6,7,8,9-hexahydro-1H-pyrrolo[3,2-h]isoquinoline; and (iii) reacting the 2,3-dioxo-2,3,6,7,8,9-hexahydro-1H-pyrrolo[3,2-h]isoquinoline obtained in step (ii) with chiral (enantiopure (R) or (S)) α-N,N-diBoc-aminoxy-γ-butyrolactone to obtain the desired chiral end product, i.e. enantiopure (R)- or (S)-2-[2-oxo-1,2,6,7,8,9-hexahydro-pyrrolo [3,2-h]isoquinolin-3-ylideneaminooxyl]-4-hydroxy-butyric acid.

3. The method of claim 1, which method further comprises the step of (b) subjecting N,N-diBoc-O-benzylhydroxylamine to hydrogenation to give N,N-diBoc-hydroxylamine;

followed by step (a) reacting enantiopure (S) or (R) α-hydroxy-γ-butyrolactone with N,N-diBoc-hydroxylamine to give enantiopure (S) or (R) α-N,N-diBoc-aminoxy-γ-butyrolactone; and followed by the sequential steps of:

(i) reacting an 8-amino-1,2,3,4-tetrahydro-isoquinoline with chloral hydrate and hydroxylamine hydrochloride to give an N-(1,2,3,4-tetrahydro-isociuinolin-8-yl)-2-hydroxyimino-acetamide;

(ii) adding sulphuric acid to the N-(1,2,3,4-tetrahydro-isoquinolin-8-yl)-2-hydroxyimino-acetamide obtained in step (i) to provide a 2,3-dioxo-2,3,6,7,8,9-hexahydro-1H-pyrrolo[3,2-h]isoquinoline; and (iii) reacting the 2,3-dioxo-2,3,6,7,8,9-hexahydro-1H-pyrrolo[3,2-h]isoquinoline obtained in step (ii) with chiral (enantiopure (R) or (S) α-N,N-diBoc-aminoxy-γ-butyrolactone to obtain the desired chiral end product, i.e. enantiopure (R)- or (S)-2-[2-oxo-1,2,6,7,8,9-hexahydro-pyrrolo[3,2-h]isoquinolin-3-ylideneaminooxy]-4-hydroxy-butyric acid.

4. The method of claim 1, which method further comprises the step of (c) converting O-benzylhydroxylamine into N,N-diBoc-O-benzylhydroxylamine using $Boc_2O$;

followed by step (b) subjecting N,N-diBoc-O-benzylhydroxylamine to hydrogenation to give N,N-diBoc-hydroxylamine;

followed by step (a) reacting enantiopure (S) or (R) α-hydroxy-γ-butyrolactone with N,N-diBoc-hydroxylamine to give enantiopure (S) or (R) α-N,N-diBoc-aminoxy-γ-butyrolactone; and followed by the sequential steps of:

(i) reacting an 8-amino-1,2,3,4-tetrahydro-isoquinoline with chloral hydrate and hydroxylamine hydrochloride to give an N-(1,2,3,4-tetrahydro-isoquinolin-8-yl)-2-hydroxyimino-acetamide;

(ii) adding sulphuric acid to the N-(1,2,3,4-tetrahydro-isoquinolin-8-yl)-2-hydroxyimino-acetamide obtained in step (i) to provide a 2,3-dioxo-2,3,6,7,8,9-hexahydro-1H-pyrrolo[3,2-h]isoquinoline; and (iii) reacting the 2,3-dioxo-2,3,6,7,8,9-hexahydro-1H-pyrrolo[3,2-h]isoquinoline obtained in step (ii) with chiral (enantiopure (R) or (S) α-N,N-diBoc-aminoxy-γ-butyrolactone to obtain the desired chiral end product, i.e. enantiopure (R)- or (S)-2-[2-oxo-1,2,6,7,8,9-hexahydro-pyrrolo[3,2-h]isoquinolin-3-ylideneaminooxyl]-4-hydroxy-butyric acid.

5. The method of claim 1, which method further comprises the step of (d) reacting enantiopure (S) or (R) α-hydroxy-γ-butyrolactone with tosyl chloride to give enantiopure (S) or (R) α-tosyloxy-γ-butyrolactone;

followed by step (c) converting O-benzylhydroxylamine into N,N-diBoc-O-benzylhydroxylamine using $Boc_2O$;

followed by step (b) subjecting N,N-diBoc-O-benzylhydroxylamine to hydrogenation to give N,N-diBoc-hydroxylamine;

followed by step (a) reacting enantiopure (S) or (R) α-hydroxy-γ-butyrolactone with N,N-diBoc followed by the sequential steps of:

(i) reacting an 8-amino-1,2,3,4-tetrahydro-isoquinoline with chloral hydrate and hydroxylamine hydrochloride to give an N-(1,2,3,4-tetrahydro-isoquinolin-8-yl)-2-hydroxyimino-acetamide;

(ii) adding sulphuric acid to the N-(1,2,3,4-tetrahydro-isoquinolin-8-yl)-2-hydroxyimino-acetamide obtained in step (i) to provide a 2,3-dioxo-2,3,6,7,8,9-hexahydro-1H-pyrrolo[3,2-h]isoquinoline; and (iii) reacting the 2,3-dioxo-2,3,6,7,8,9-hexahydro-1H-pyrrolo[3,2-h]isoquinoline obtained in step (ii) with chiral (enantiopure (R) or (S)) α-N,N-diBoc-aminoxy-γ-butyrolactone to obtain the desired chiral end product, i.e. enantiopure (R)- or (S)-2-[2-oxo-1,2,6,7,8,9-hexahydro-pyrrolo[3,2-h]isoquinolin-3-ylideneaminooxy]-4-hydroxy-butyric acid.

6. A method of preparing a chiral (±) isomer of an indole-2,3-dione-3-oxime compound, which method comprises the sequential steps of:

(i) reacting 4-(8-amino-2-methyl-1,2,3,4-tetrahydro-isoquinolin-5-yl)-N,N-dimethyl-benzenesulfonamide and hydroxylamine hydrochloride to give N-[5-(4-dimethylsulfamoyl-phenyl)-2-methyl-1,2,3,4-tetrahydro-isoquinolin-8-yl]-2-hydroxyimino-acetamide;

(ii) adding sulphuric acid to the N-[5-(4-dimethylsulfamoyl-phenyl)-2-methyl-1,2,3,4-tetrahydro-isoquinolin-8-yl]-2-hydroxyimino-acetamide obtained in step (i) to provide N,N-dimethyl-4-(8-methyl-2,3-dioxo-2,3,6,7,8,9-hexahydro-1H-pyrrolo[3,2-h]isoquinolin-5-yl)-benzenesulfonamide; and (iii) reacting the N,N-dimethyl-4-(8-methyl-2,3-dioxo-2,3,6,7,8,9-hexahydro-1H-pyrrolo[3,2-h]isoquinolin-5-yl)-benzenesulfonamide obtained in step (ii) with chiral (enantiopure (R) or (S)) α-N,N-diBoc-aminoxy-γ-butyrolactone to obtain the desired chiral end product, i.e. enantiopure (R)- or (S)-2-[5-(4-dimethylsulfamoyl-phenyl)-8-methyl-2-oxo-1,2,6,7,8,9-hexahydro-pyrrolo[3,2-h]isoquinolin-3-ylideneaminooxy]-4-hydroxy-butyric acid, followed by recovery of the desired end product.

7. A method of preparing the chiral (±) isomers of indole-2,3-dione-3-oxime compounds in accordance with claim 1, which method comprises the sequential steps of:

(i) reacting an 8-amino-1,2,3,4-tetrahydro-isoquinoline of the formula

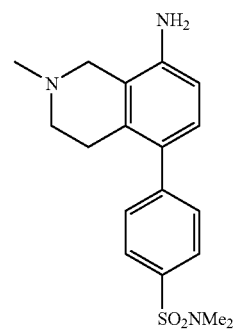

with chloral hydrate and hydroxylamine hydrochloride to give an N-(1,2,3,4-tetrahydro-isoquinolin-8-yl)-2-hydroxy-imino-acetamide of the formula

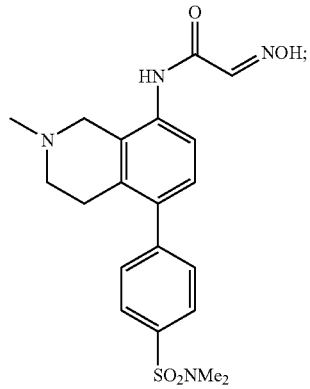

(ii) adding sulphuric acid to the N-(1,2,3,4-tetrahydro-isoquinolin-8-yl)-2-hydroxyimino-acetamide obtained in step (i) to provide a 2,3-dioxo-2,3,6,7,8,9-hexahydro-1H-pyrrolo[3,2-h]isoquinoline of the formula

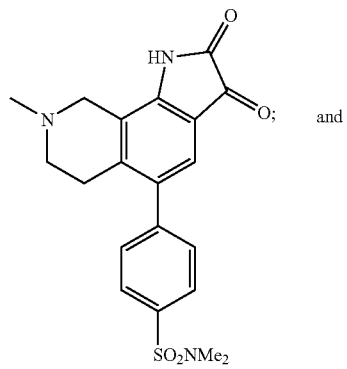

and (iii) reacting the 2,3-dioxo-2,3,6,7,8,9-hexahydro-1H-pyrrolo[3,2-h]isoquinoline obtained in step (ii) with chiral (enantiopure (R) or (S)) α-N,N-diBoc-aminoxy-γ-butyrolactone of the formula

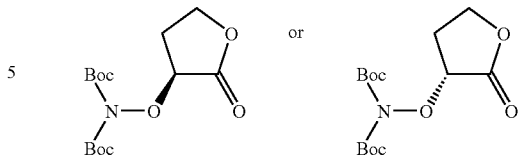

to obtain the desired chiral enantiopure (R)- or (S)-2-[2-oxo-1,2,6,7,8,9-hexahydro-pyrrolo[3,2-h]isoquinolin-3-ylidene-aminooxy]-4-hydroxy-butyric acid of the formula (IVA) or (IVB)

(IVA)

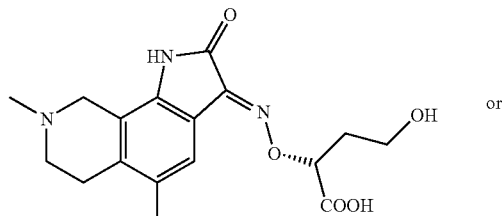

or (IVB)

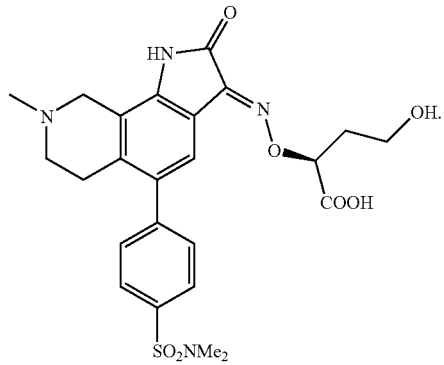

* * * * *